United States Patent [19]

Berliner et al.

[11] 4,222,390

[45] Sep. 16, 1980

[54] SPHYGMOMANOMETER GAUGE AND METHOD OF USE FOR BLOOD PRESSURE MEASUREMENT

[75] Inventors: Emanuel Berliner, Valley Stream; Elwyn Spiegel, New York, both of N.Y.; Nobuo Kaneda, Tokyo, Japan

[73] Assignee: Bristoline, Inc., Freeport, N.Y.

[21] Appl. No.: 928,565

[22] Filed: Jul. 27, 1978

[51] Int. Cl.³ .............................................. A61B 5/02
[52] U.S. Cl. .................................... 128/677; 128/672; 128/900; 116/296; 73/712
[58] Field of Search ............... 128/677, 681, 900, 675, 128/678, 672; 116/271, 296, 291, DIG. 37, 328, 329, DIG. 3, DIG. 25; 73/712, 700

[56] References Cited

U.S. PATENT DOCUMENTS

| 2,848,973 | 8/1958 | Steins | 116/296 |
|---|---|---|---|
| 3,662,394 | 5/1972 | Dudler | 128/900 |
| 3,901,217 | 8/1975 | Clark | 128/900 |

Primary Examiner—Willis Little

[57] ABSTRACT

A sphygmomanometer gauge included a stationary dial having graduations indicative of different blood pressure values. A needle is turnable about an axis over the dial in response to changes in air pressure generated in the sphygmomanometer. A pair of adjustable members are mounted on the gauge for turning movement in either circumferential direction about the axis. Each adjustable member has an access portion which extends through the gauge housing to thereby permit independent and manual turning. A systolic indicator and a diastolic indicator are respectively mounted on the adjustable members for turning movement with the latter. Each indicator is operative to simultaneously indicate both a single value and a range of values of blood pressure. A user may either manually preset each of the indicators to respective positions corresponding to predetermined medically-established pressure norms for subsequent comparison purposes during the blood pressure measurement, or the user may manually set each of the indicators to its respective pressure measuring position, as observed during the blood pressure measurement for subsequent leisurely recordation.

23 Claims, 8 Drawing Figures

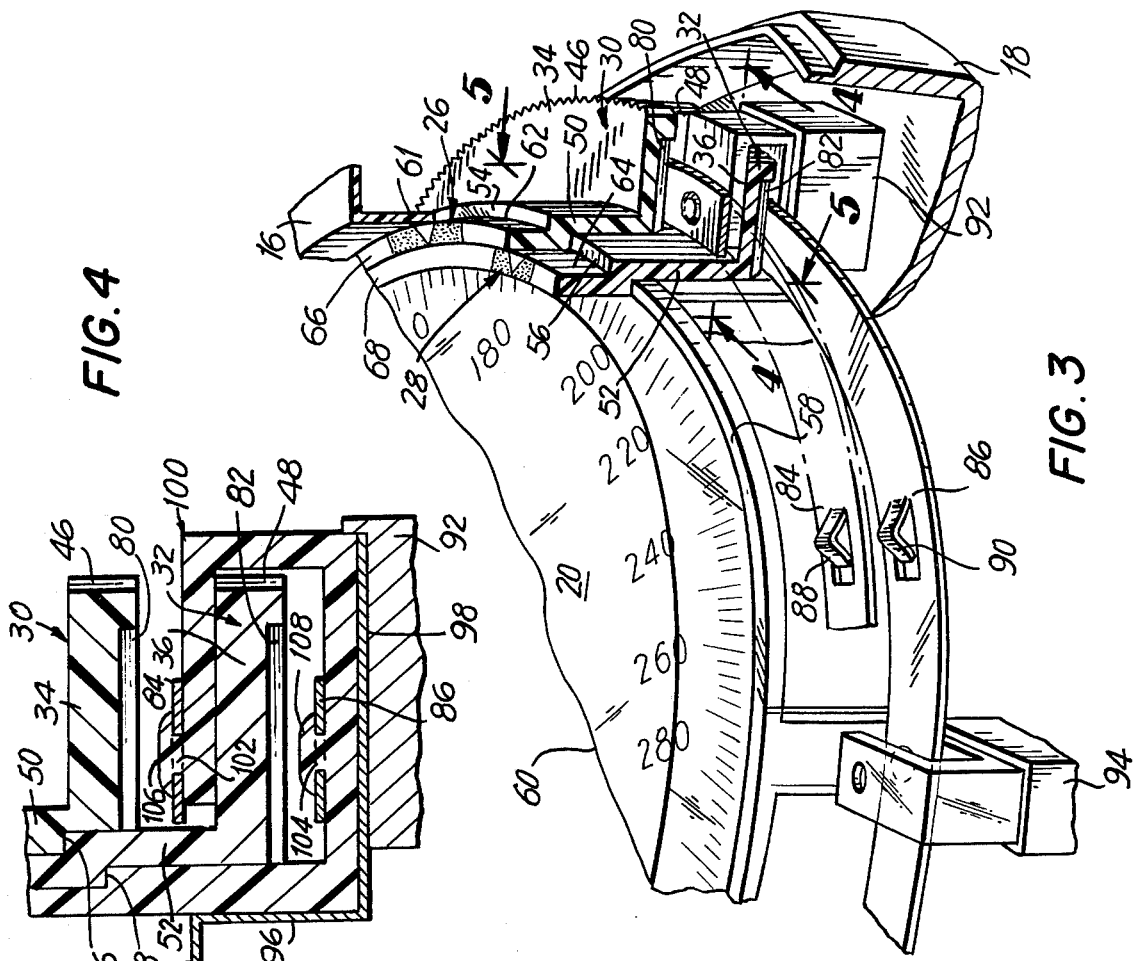
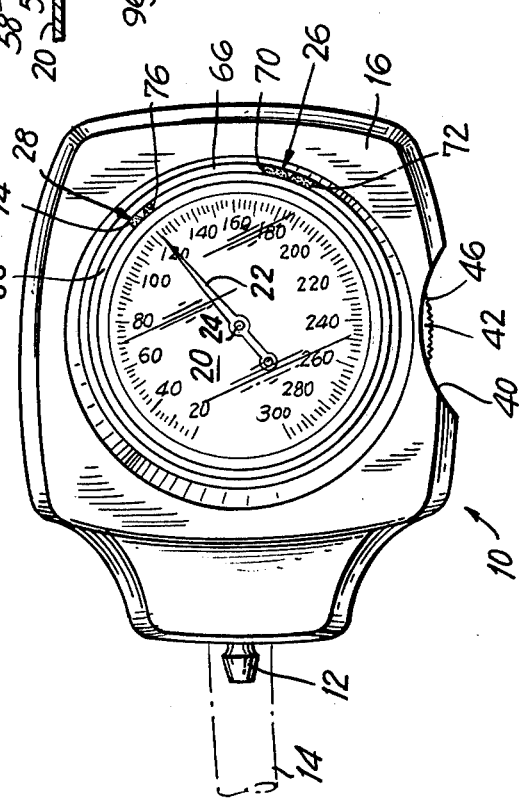
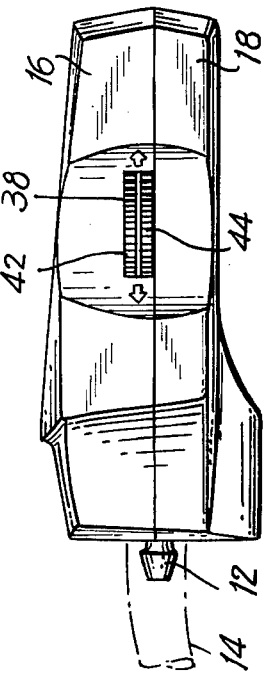

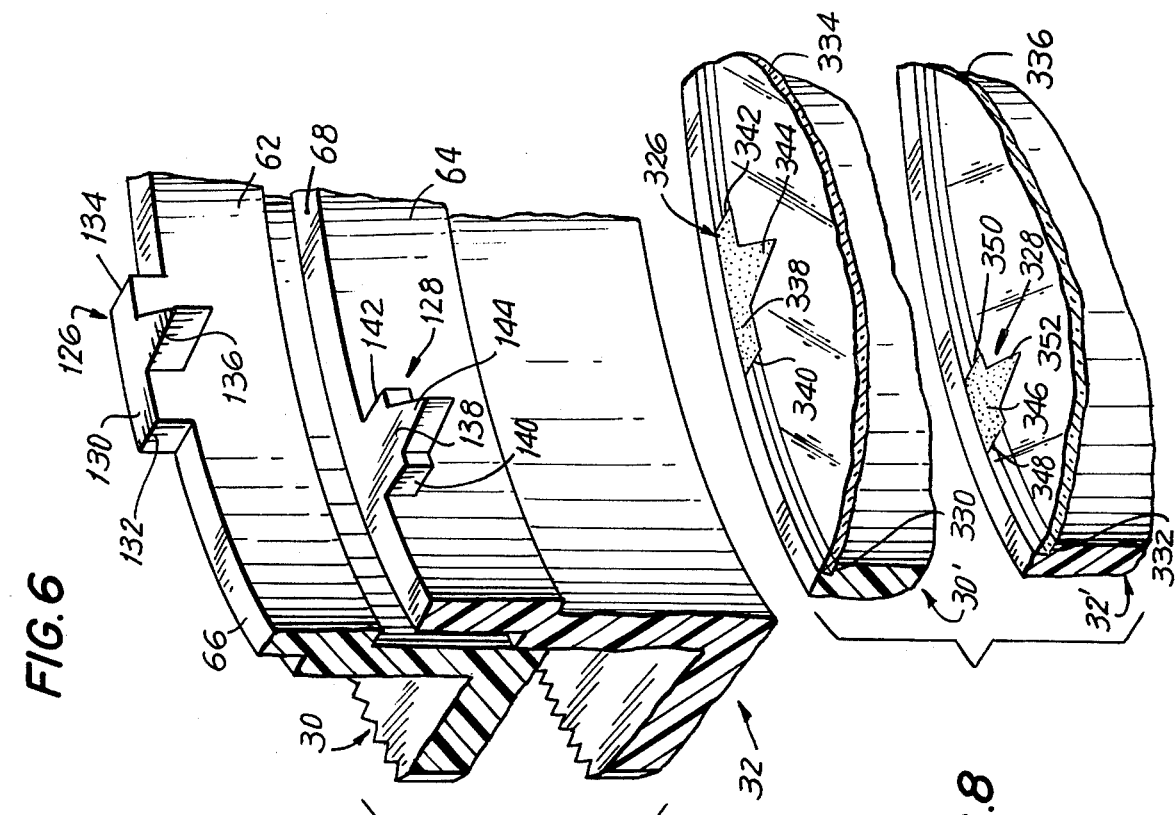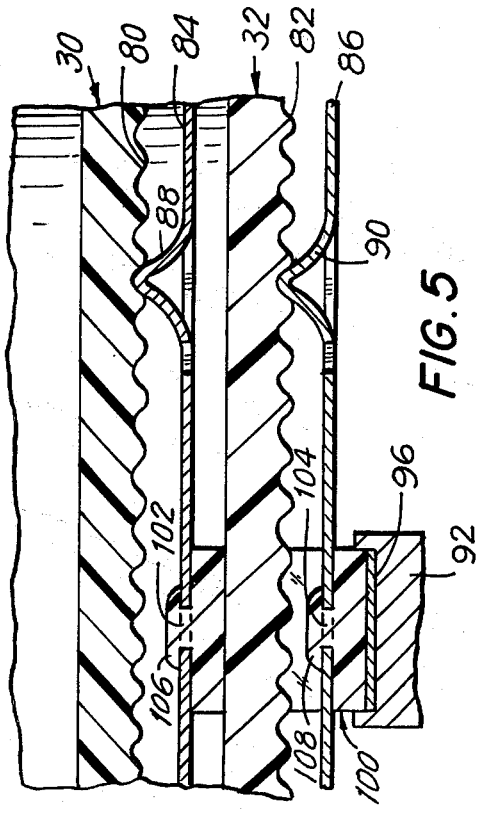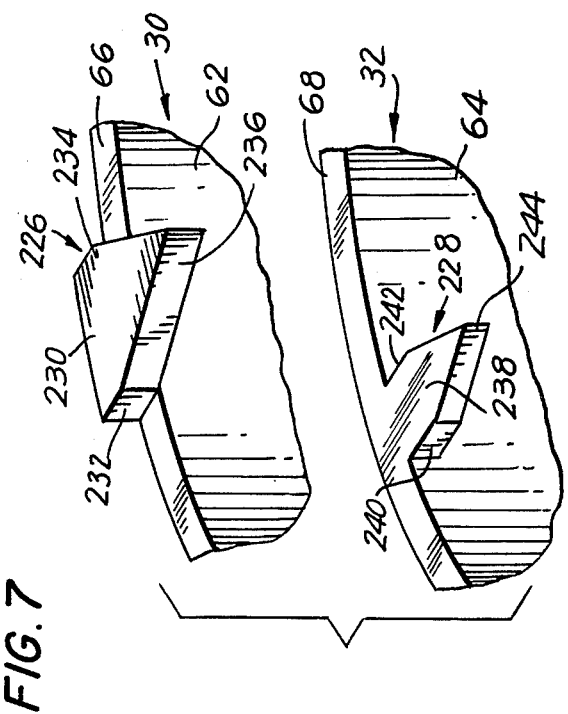

SPHYGMOMANOMETER GAUGE AND METHOD OF USE FOR BLOOD PRESSURE MEASUREMENT

BACKGROUND OF THE INVENTION

1. Field of the Invention

The present invention generally relates to sphygmomanometers and, more particularly, to a sphygmomanometer gauge for indicating systolic and diastolic blood pressures. Still more particularly, the present invention relates to a method of indicating actual systolic and diastolic blood pressure readings during the blood pressure measurement for subsequent leisurely recordation and, yet more particularly, to a method of comparing actual systolic and diastolic blood pressure readings with predetermined medically-established pressure norms, as preset on the gauge.

2. Description of the Prior Art

A sphygmomanometer is a clinical apparatus for measuring the blood pressure. It comprises an inflatable rubber cuff which is wrapped around the upper arm of a patient. The cuff is connected by rubber tubing to a resilient hand bulb and is inflated by repetitively squeezing the bulb. A pressure-indicating manometer device or pressure gauge has a pressure-calibrated dial and a pressure needle, which is movable over the latter. The needle is operatively connected by a rubber tubing to the cuff, and is movable in response to changes in air pressure in the cuff. A manually operable bleeder valve is provided to slowly bleed air from the inflated cuff.

In use, sufficient pressurized air is pumped into the rubber cuff until the inflated cuff tightens sufficiently to occlude the brachial artery in the upper arm, i.e., stop the blood flow therein. A stethescope is applied over the artery below the cuff, and air is gradually allowed to escape through the bleeder valve from the cuff until a pulsing rush of blood can be heard. The pressure needle of the gauge at this point indicates the systolic pressure or the highest pressure in the arteries during contraction of the heart.

As deflation of the cuff continues, the air pressure within the cuff falls, and the needle successively indicates lower and still lower pressure readings. The diastolic pressure, or lowest pressure in the artery during diastole, or relaxation of the heart muscle between beats, is indicated by the needle on the dial when the last sound of the disappearing pulse is heard, i.e., when the rush of blood becomes inaudible. Upon further deflation of the cuff, the needle returns from its two previous measurement positions to its starting position. The normal systolic reading of an adult varies from 110 to 130 or 140 mm Hg. Normal diastolic readings vary from 60 to 90 mm Hg.

It is often difficult for an individual taking his own blood pressure to accurately read and note the systolic and diastolic blood pressures during the blood pressure measurement due to the fact that the individual must simultaneously regulate the air bleeder valve, carefully observe the pressure needle as it quickly moves over the dial, and listen to the sounds of the pulses through the stethescope. Moreover, even skilled personnel, who are trained in the art of taking blood pressure measurements, must either make a mental or very rapid written note of the systolic pressure reading at the appropriate time before the time approaches when the diastolic pressure must be read.

In order to eliminate the drawbacks involved in reliance upon a faulty memory and/or in making very hasty written, and possibly illegible, notes of the systolic and diastolic blood pressure readings, the prior art has proposed automatically-operated sphygmomanometer gauges which have two recording needles in addition to the main pressure needle. The main pressure needle, according to one proposal, automatically carries the two recording needles over the dial until the user decides to manually lock the respective recording needles in position. The prior art has also proposed a pair of recording needles which are moved automatically in response to pressure and electrical pulses and are locked automatically in their measured positions by a rachet-pawl-solenoid. Examples of such automatically-operated sphygmomanometer gauges can be had by reference to U.S. Pat. Nos. 3,901,217 and 3,056,401.

However, such automatically-operated gauges have not proven altogether satisfactory, inasmuch as the gauges require a considerable number of parts, are complex in construction, are expensive to manufacture, are cumbersome and are not altogether reliable or accurate. Moreover, all of the known automatically-operated sphygmomanometer gauges which separately record systolic and diastolic blood pressures utilize a pair of recording needles, each of which only records a single valve of blood pressure. It is highly desirable for a consumer-type user, as opposed to highly trained medical personnel, to be readily informed of a range of values of systolic and diastolic blood pressures, either in advance of or during the blood pressure measurement.

SUMMARY OF THE INVENTION

1. Objects of the Invention

Accordingly, it is a general object of the present invention to overcome the aforementioned drawbacks of the prior art.

Another object of the present invention is to provide a new and useful sphygmomanometer gauge for use with a sphygmomanometer of the self-donning type, which may be conveniently donned and easily operated by a consumer.

Still another object of the present invention is to eliminate the necessity of carefully observing the gauge while taking one's blood pressure.

Yet another object of the present invention is to eliminate measurement recording errors involved in reliance upon a faulty memory.

An additional object of the present invention is to eliminate measurement recording errors involved in making hasty and perhaps illegible written notes during the blood pressure measurement.

Another object of the present invention is to simplify the construction of a sphygmomanometer gauge for indicating both systolic and diastolic blood pressures.

An additional object of the present invention is to reliably inform a user in advance of the blood pressure measurement of a range of values of blood pressure which correspond to medically-established norms for subsequent comparison purposes during the blood pressure measurement.

Still another object of the present invention is to reliably inform a user during the blood pressure measurement of a range of values for subsequent leisurely recordation purposes.

Yet another object of the present invention is to simultaneously indicate both the value and the range of the systolic blood pressure and the value and the range of the diastolic blood pressure for subsequent leisurely recordation purposes.

Another object of the present invention is to provide a novel method of comparing actual systolic and diastolic blood pressure readings with predetermined medically-established pressure norms.

Another object of the present invention is to provide a method of reliably indicating actual systolic and diastolic blood pressure readings for subsequent leisurely recordation.

2. Features of the Invention

In keeping with these objects and others which will become apparent hereinafter, one feature of the invention resides, briefly stated, in a method of, and sphygmomanometer gauge for, indicating systolic and diastolic blood pressures to a user of a sphygmomanometer, particularly of the self-donning type. The gauge comprises a housing, a pressure-calibrated dial mounted on the housing, and a movable pressure needle mounted on the housing for movement over the dial in response to changes in air pressure generated in the sphygmomanometer along a first path in which both a systolic pressure measuring position and a diastolic pressure measuring position are located.

In accordance with the present invention, a manually movable systolic indicator and a manually movable diastolic indicator are both mounted on the housing for movement relative to the latter. The present invention further includes a first and a second user-operated means or adjustable members for manually and adjustably moving the systolic and diastolic indicators respectively along a second and a third path, each spaced from and adjacent to the first path.

In operation, the user may elect to either manually preset each of the indicators to respective positions corresponding to predetermined medically-established pressure norms for subsequent comparison purposes during the blood pressure measurement, or the user may elect to manually set each of the indicators to its respective pressure-measuring position as observed during the blood pressure measurement for subsequent leisurely recordation.

In the first-mentioned manual "preset" mode of operation, the user manually presets the systolic indicator to a position on the dial which corresponds to the predetermined medically-established systolic pressure norm for that individual. Thereupon, the user manually presets the diastolic indicator to a position on the dial which corresponds to the predetermined medically-established diastolic pressure norm for that individual. Subsequently, the user compares the observed systolic and diastolic positions on the pressure needle of the gauge as it moves over the dial with the preset positions of the systolic and diastolic indicators.

In the second-mentioned manual "set" mode of operation, the user first observes the movement of the pressure needle of the gauge over the dial. Once the systolic pressure reading is observed, the systolic indicator is manually set at this position during the blood pressure measurement. Again, once the diastolic pressure reading is observed, the diastolic indicator is manually set at its corresponding position during the blood pressure measurement. Subsequently, the user may, at his leisure, refer to the set positions of the two indicators in order to properly record the systolic and diastolic blood pressure readings in a slower, more accurate, and more reliable manner, without the exigencies of time being a relevant factor.

It will thus be readily understood that the above-described manually-operated device of the present invention not only functions to eliminate measurement recording errors due to reliance upon poor memory and/or upon hastily written notes, but also reliably informs the user, in advance, of the predetermined medically-established pressure norms. The manual operation of the indicators thereby overcomes the automatic operation of the prior art sphygmomanometer gauges which, of course, cannot be preset in advance or adjusted in any manner whatsoever during the blood pressure measurement.

In accordance with yet another feature of the present invention, each indicator is operative for simultaneously indicating not only a single value, but also a range of values of blood pressure. In the manual "preset" mode of operation, the user compares the observed systolic and diastolic blood pressure readings not only with single preset positions of the respective indicators, but also with respective ranges. For some purposes, and particularly for consumer purposes, it is not necessary for a user to known his blood pressure readings exactly; that is, it may be sufficient for the user to known that his blood pressure readings fall within a predetermined range. In this case, it will be readily understood that the provision of a range on each of the indicators results in the advantage that the consumer-type user need not so carefully observe the precise scale reading on the dial.

The novel features which are considered as characteristic for the invention are set forth in particular in the appended claims. The invention itself, however, both as to its construction and its method of operation, together with additional objects and advantages thereof, will best be understood from the following description of specific embodiments when read in connection with the accompanying drawing(s).

BRIEF DESCRIPTION OF THE DRAWINGS

FIG. 1 is a top view of a preferred embodiment of a sphygmomanometer gauge, and diagramatically shows the rubber tubing for connection to the other parts of the sphygmomanometer;

FIG. 2 is a side view of the gauge of FIG. 1;

FIG. 3 is an enlarged, perspective, partially sectioned, and partially cut-away view of the gauge of FIG. 1;

FIG. 4 is a greatly enlarged, partially broken away, sectional view taken on line 4—4 of FIG. 3;

FIG. 5 is a greatly enlarged, partially broken away, sectional view as taken on line 5—5 of FIG. 3;

FIG. 6 is a perspective, exploded view of two adjustable indicators for another preferred embodiment of a sphygmomanometer gauge, the remaining parts of the gauge being removed for the sake of clarity;

FIG. 7 is a view generally analogous to FIG. 6 and shows still another preferred embodiment of a sphygmomanometer gauge; and FIG. 8 is a view generally analogous to FIG. 7 and shows yet another preferred embodiment of a sphygmomanometer gauge.

DETAILED DESCRIPTION OF THE PREFERRED EMBODIMENTS

Referring now to the drawings, reference numeral 10 in FIG. 1 generally illustrates a pressure-indicating device or pressure gauge of an aneroid sphygmomanometer. A tubular nozzle 12 projects from the gauge 10, and one end of a diagramatically (dashed line) illustrated rubber tubing 14 is mounted in air-tight, frictional-type engagement over the nozzle 12 to thereby establish air communication between a non-illustrated bellows chamber within the gauge and a non-illustrated conventional cuff which is inflatable by a non-illustrated conventional resilient hand bulb pump. Specific structural and functional details of the cuff, the hand bulb pump, the rubber tubing and the bellows chamber are not believed to be necessary and, therefore, have not been provided because they are well known in the art of sphygmomanometers and, in fact, form no essential part of the present invention. Such conventional details of a sphygmomanometer can be found by reference to such patents as U.S. Pat. Nos. 3,901,217 and 3,056,401, and by reference to co-pending U.S. Pat. Application Ser. No. 859,746, filed Dec. 12, 1977, in the name of Scachio Enatsu, entitled "Fine-Adjusting Arrangement for a Sphygmomanometer," and now allowed.

The gauge 10 comprises a two-part housing composed of a top part 16 and a bottom part 18, each part being constituted of either synthetic plastic or metal material. As best shown in FIG. 1, each housing part is formed with a sculptured, streamlined shape, such that the housing is wider at its central region and slightly narrower at its tapered end regions. The steamlined shape of the housing permits it to be easily grasped and held in the palm of a user.

The gauge 10 further comprises a pressure-calibrated stationary dial mounted in a generally circular aperture formed at the wide central region of the housing. The dial includes a generally circular scale 20 having a plurality of spaced-apart marks or graduations respectively indicative of different values of blood pressure. As illustrated in FIG. 1, the dial scale 20 is calibrated in standard circular fashion from 20 mm Hg to 300 mm Hg, with every 20 mm Hg subdivision being individually marked with a number, and with every two mm Hg being individually denoted by a graduation mark. Other calibration scales are, of course, possible.

The gauge 10 still further comprises a pointer or pressure needle 22 mounted on the housing for turning movement over the dial scale 20 about an axis, as defined by shaft 24, on which the needle 22 is mounted. The needle 22 is turned in response to changes in air pressure generated in the sphygmomanometer. Specific structural and functional details of the operative connection between the non-illustrated cuff, the rubber tubing 14, the nozzle 12 and the non-illustrated bellows chamber within the gauge are not believed to be necessary and, therefore, have not been provided because they are already known in the art. The specific details of this operative connection can be found by reference to the aforementioned co-pending U.S. Pat. application Ser. No. 859,746, the entire contents of which are hereby incorporated by reference in the present application.

It is believed to be sufficient to point out that the needle 22 is moved along a first multi-position circular path from a starting null position, preferably a floating position centrally located between the 20 mm Hg and the 300 mm Hg marks on the dial scale, in one circumferential direction to an end position which corresponds to sufficient air pressure being pumped into the cuff by the hand bulb to occlude the brachial artery for that particular patient. Upon bleeding the non-illustrated bleeder valve, the pressure in the inflated cuff falls and the needle 22 moves back in opposite circumferential direction from the end position to the systolic blood pressure position (at the time when the pulsing rush of blood can be heard), and thereupon, to the diastolic blood pressure measuring position (at the time when the pulsing rush of blood can no longer be heard), and ultimately returns to the starting position.

In order to overcome the above-noted unreliability inherent in reliance upon memory and upon hastily written notes, the present invention proposes manually-movable systolic indicator means 26 and manually-movable diastolic indicator means 28. The indicator means 26, 28 are respectively mounted on first and second user-operated means 30, 32 for turning movement about the turning axis at 24. As shown in the FIGS. 1–5 embodiment, both user-operated means 30, are adjustable members of annular configuration, the adjustable members being movable along second and along third circular paths which are spaced from, adjacent to and concentric with the aforementioned first circular path of the needle 22.

Adjustable members 30, 32, respectively, have circular base walls, 34, 36, respective portions of which extend outwardly of the housing through a side port 38. Side port 38 is located in an arcuate cut-out 40 formed at the wide central region of the housing. The outwardly-extending circumferential portions of the bases 34, 36, respectively, constitute manually grippable or access portions 42, 44, which permit a user to gain ready access and to thereby independently manually turn the respective adjustable members in either circumferential direction, as indicated by the arrows in FIG. 2, about the axis at 24. A roughened exterior surface, e.g., knurlings 46, 48, is formed on the periphery of each base wall 34, 36 to thereby facilitate manual gripping of the access portions 42, 44.

Adjustable members 30, 32 further respectively have tubular, cylindrical walls 50, 52 extending in axial direction from the base walls 34, 36, and also respectively have circular, radially extending walls or shoulders 54, 56. The upper surface of shoulder 54 slidably engages the projection 61 which extends downwardly from the top housing part 16. The lower surface of shoulder 54 slidably engages the upper surface of shoulder 56. The lower surface of shoulder 56 slidably engages a shelf 58 of the crystal 60. Adjustable member 30, 32 are thus stacked one above another in juxtaposed sliding abutting relationship. In order to keep the coefficient of sliding friction between the adjustable nested members 30, 32 to a minimum value, the radial extensions of each shoulder 54, 56 is kept very small, typically, less than one-sixteenth of an inch. Moreover, the adjustable members are preferably made of smooth, molded synthetic plastic material. By keeping friction to a mimimum value, manual movement of any one selected adjustable member will not be undesirably transmitted to the other adjustable member.

Adjustable members 30, 32 still further respectively have additional cylindrical walls 62, 64 which extend in an axial direction from the shoulders 54, 56 and which are concentric with cylindrical walls 50, 52. The additional walls 62, 64 are spaced radially apart from each other, and both additional walls fit snugly within the circular aperture formed in the top part 16 at the wide central region of the housing. As best shown in FIG. 3, systolic indictor means 26 is mounted on the axial end face or rim 66 of the additional cylindrical wall 62 of the radially outer adjustable member 30, whereas the diastolic indicator means 28 is separately mounted on the axial end face or rim 68 of the additional cylindrical wall 64 of the radially inner adjustable member 32.

Rims 66, 68 are generally formed with a predetermined color, e.g., beige or off-white. Systolic and diastolic indicator means 26, 28 are comprised of a generally rectangular zone having a color which contrasts with said predetermined color, e.g., systolic indicator 26 may be colored red, whereas the diastolic indicator 28 may be colored green. Each generally rectangular zone is indicated by stippling in the drawings, and it will be noted that each rectangular zone is not truly rectangular, but has a pair of arcuate longer edges, whose center of curvature is located at the axis at 24, and a pair of radially-extending shorter side edges. As best shown in FIG. 1, systolic indicator 26 has side edges 70, 72 and diastolic indicator 28 has side edge 74, 76. These side edges indicate the outer limits of a range of values of blood pressure on the dial scale 20, and thus constitute range-indicating means.

Systolic and diastolic indicator means 26, 28 also each comprise a generally triangular zone having a color which contrasts with the contrasting color of the respective generally rectangular zones. The apex of each triangular zone points inwardly towards the axis at 24, and the apex thus constitutes single value-indicating means. The triangular zones are located centrally between the respective side edges of the various generally rectangular zones. The color of each triangular zone may match the predetermined color of the rims 66, 68, if desired. It will be expressly understood that the specifically identified colors mentioned above merely exemplify, and are not intended to limit, the scope of the present invention in any manner whatsoever.

It will be noted that the circumferential distance between the side edges 70, 72 of the systolic indicator 26 is approximately two times as long as the circumferential distance between the side edges 74, 76 of the diastolic indicator 28. We have found it advantageous to make the circumferential distance between side edges 70, 72 extend over a spacing corresponding to 20 mm Hg on the dial face, and to make the circumferential distance between side edges 74, 76 extend over a spacing corresponding to 10 mm Hg. The anticipated larger tolerance in the systolic blood pressure measurement is thus practically embodied in the wider range to be indicated by the systolic indicator, as compared to the correspondingly narrower range to be indicated by the diastolic indicator.

Turning now to FIG. 6, reference numerals 126 and 128 respectively identify a pair of systolic and diastolic indicator means which may be used as fully functional equivalents of the indicators 26, 28 of the embodiment of FIGS. 1-5. Systolic indicator 126 comprises a generally parallelpiped-shaped flange portion 130 which projects upwardly in an axial direction from rim 66 of circular wall 62. Flange portion 130 has a pair of side walls 132, 134 which respectively indicate the outer limits of the systolic range. Systolic indicator 126 also comprises a generally triangular-shaped flange portions 136 which extends inwardly in a radial direction from portion 130. The apex of flange portion 136 points towards the axis at 24, and thus indicates a single value of blood pressure. The base wall of flange portion 136 extends over a part of the circumferential distance between side walls 132, 134. The flange portion 136 extends downwardly in an axial direction, but terminates either short of or substantially at the level at which rim 66 is located.

Diastolic indicator 128 comprises a generally parallelepiped-shaped flange portion 138 which projects inwardly in a radial direction from the cylindrical wall 64. Flange portion 138 has a pair of side walls 140, 142, which indicate the outer limits of the diastolic range. Diastolic indicator 128 also comprises a generally triangular-shaped flange portion 144 which projects inwardly in a radial direction from the flange portion 138. The apex of flange portion 138 points towards the axis, and thus constitutes a single value-indicating means. The base wall of the flange portion 138 extends over a part of the circumferential distance between side walls 140, 142. All portions of the diastolic indicator 128, which are of one piece with adjustable member 32, are located below all portions of the systolic indicator 126, which are of one piece with adjustable member 30, to thereby provide mechanical clearance during turning movement of the adjustable members 30, 32, and to prevent mutual mechanical interference.

Turning now to FIG. 7, reference numerals 226 and 228 respectively identify systolic and diastolic indicator means which may be used as fully functional equivalents of the indicator means 26, 28 or 126, 128. Systolic indicator 226 comprises a generally parallepiped-shaped flange portion 230 which projects upwardly in an axial direction from the circumferential wall 62. Flange portion 230 has a pair of side walls 232, 234 which indicate the outer limits of the systolic range. Systolic indicator 226 also comprises a generally triangular-shaped flange portion 236 which projects inwardly in a radial direction from the flange portion 230. The apex of flange portion 236 points toward the axis. The base wall of the flange portion 236 extends over the entire circumferential distance between side walls 232, 234. All portions of the systolic indicator 226 are located above rim 66.

Diastolic indicator 228 comprises a generally parallelepiped shaped flange portion 238 which projects inwardly in a radial direction from the cylindrical wall 64. Flange portion 238 has a pair of side walls 240, 242 which indicate the outer limits of the diastolic range. Diastolic indicator 228 also comprises a generally triangular-shaped flange portion 244 which projects inwardly in a radial direction from the flange portion 238. The apex of flange portion 244 points toward the axis. The base wall of flange portion 244 extends over the entire circumferential distance between side walls 240, 242. All portions of the diastolic indicator 228 are located below rim 68 to thereby prevent mutual mechanical interference.

Turning now to FIG. 8, reference numerals 326, 328 respectively identify systolic and diastolic indicator means which may be used as fully functional equivalents of the indicator means 26, 28 or 126, 128 or 226, 228. In this embodiment, annular members 30', 32' are respectively provided with circular lips 330, 332. Transparent dial covers or circular watch-type crystals 334, 336 are fixedly mounted on each lip in a juxtaposed, stacked relationship relative to the dial face, i.e., crystal 334 is mounted at a higher elevation over the dial as compared to crystal 336.

Systolic indicator 326 is mounted at a portion of the border region of crystal 334, and comprises a colored zone on the otherwise non-colored, transparent crystal 334. This zone includes a generally rectangular area 338 having radially-extending side edges 340, 342, to thereby indicate a blood pressure range, and also includes a generally triangular area 344 having a radially-extending apex to thereby indicate a single blood pressure value.

Diastolic indicator 328 is mounted at a portion of the border region of crystal 336, and comprises a differently colored zone on the otherwise non-colored, transparent crystal 336. This colored zone includes a generally rectangular area 346 having radially-extending side edges 348, 350, and also includes a generally triangular area 352 having a radially-extending apex.

For each of the embodiments of FIGS. 6, 7 and 8, it has been diagramatically shown that the ranges for systolic indicators 126, 226 and 326 are generally on the order of two times as large as the ranges for the diastolic indicators 128, 228 and 328, respectively.

Returning now to the embodiment of FIGS. 1–5, we have found it desirable to add a very slight frictional drag on each adjustable member 30, 32, to thereby provide a "mechanical feel" for the user. At the same time, we have additionally found it desirable to generate a clicking-type sound during manual movement of each adjustable member, to thereby provide "auditory feel" for the user. In order to obtain these desirable features, a first set of teeth 80 is arranged along an annulus on the underside of base 34, and a second set of teeth 82 is arranged along an annulus on the underside of base 36. As best shown in FIG. 5, each tooth of teeth sets 80, 82 has rounded edges.

A pair of annular resilient detent plates or spring pawl plates 84, 86 are respectively mounted below bases 34, 36 to respectively cooperate with teeth sets 80, 82. Each plate is preferably constituted of resilient metal material, and has a plurality of stamped-out spring pawls, spaced in a circumferential direction, about the respective plate. One such spring pawl on plate 84 is identified by reference numeral 88, and another such spring pawl on plate 86 is identified by reference numeral 90. Each spring pawl has a rounded crest which is adapted to easily cam in and cam out of the respective rounded teeth of sets 80, 82 when the adjustable members 30, 32 are turned in either requisite circumferential direction.

Each plate 84, 86 is anchored against unauthorized displacement during movement of the adjustable members. To this end, a plurality of stationary mounting blocks, only two of which are shown and identified by reference numerals 92, 94, are spaced about the axis in a fixed position on the lower housing part 18. The dial has a scale 20 and a plurality of L-shaped legs which depend from the latter, which are spaced about the axis and which are lodged in recesses formed in the blocks. For example, leg 96 is lodged in recess 98 in block 92.

The transparent crystal 60 comprises a circular portion which overlies the circular scale 20, and also comprises a plurality of J-shaped legs depending therefrom, spaced about the axis and lodged in the recesses formed in the blocks directly above the L-shaped legs of the dial. For example, J-shaped leg 100 is lodged in recess 98 above L-shaped leg 96 in block 92. In this manner, both the dial and the crystal are stationarily mounted relative to the housing 10.

As for the anchoring of the pawl plates 84, 86, a plurality of axially-extending projections, which are of one piece with the plates and which are spaced in a circumferential direction about the latter, extend upwardly through a corresponding plurality of holes formed in the pawl plates. Each projection has a peen-type or deformable head which can be easily upset into a deformed configuration, to thereby fixedly secure the plates to stationary positions. As best shown in FIGS. 4–5, representative projections 102, 104, extend through holes formed in plates 84, 86, and have peened-over heads 106, 108 to secure the plates.

In the preset mode of operation, the user manually presets the systolic indicator by moving the appropriate adjustable member to a position corresponding to the predetermined medically-established systolic pressure norm for that particular user, and thereupon manually presets the diastoic indicator by moving the other appropriate adjustable member to another position corresponding to the predetermined medically-established diastolic pressure norm for that particular user. Of course, not only the particular single value for that user is indicated, but also the particular range of values. During the movement of the adjustable members, each spring pawl, which previously cammed in a respective tooth due to its own inherent resilience to thereby lock the respective adjustable member in position with a moderate restoring force, is now cammed out of the respective tooth when the force exerted on the respective adjustable member is greater than the aforementioned restoring force. During this manual movement, the user will hear the generated clicking-type sounds. During the blood pressure measurement, the user observes the movement of the needle 22 and compares the observed systolic and diastolic positions with the preset positions.

The purpose and method of the present invention thereby provides a true consumer instrument which provides a quick visual indication of the reading, particularly to the individual who takes his own blood pressure. The width or spread of each range would correspond to what most physicians consider to be an average amount of leeway in the blood pressure measurement. All the individual using the pressure gauge has to do is preset the adjustable members at their correct positions, and, provided the needle falls within the respective ranges of the indicators, he would then know that he was in a "safety" area.

In the set mode of operation, the user first observes the needle 22 move between the systolic and diastolic pressure measuring positions. During this time, the user manually sets the systolic and diastolic indicators to the observed measuring positions. Subsequent to the blood pressure measurement, the user may refer to the set positions of the indicators for leisurely recordation.

It will be understood that each of the elements described above, or two or more together, may also find a useful application in other types of applications differing from the types described above.

While the invention has been illustrated and described as embodied in sphygmomanometer gauge and method of use for blood pressure measurement, it is not intended to be limited to the details shown, since various modifications and constitutent changes may be made with departing in any way from the spirit of the present invention. For example, the spring pawls may be replaced by a plurality of upwardly projecting protuberances of resilient synthetic plastic material.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. In an apparatus for measuring blood pressure, a sphygmomanometer gauge for indicating systolic and diastolic blood pressures to a user, comprising:
   (a) a housing;
   (b) a pressure-calibrated dial mounted on said housing, said pressure-calibrated dial including a scale having a plurality of spaced-apart graduations respectively indicative of different values of blood pressure;
   (c) a movable pressure needle mounted on said housing for movement over said pressure-calibrated dial in response to changes in air pressure generated in the apparatus along a first path in which both a systolic pressure measuring position and a diastolic pressure measuring position are located;
   (d) manually-movable systolic indicator means mounted on said housing for movement relative to the latter;
   (e) manually-movable diastolic indicator means also mounted on said housing for movement relative to the latter;
   (f) first user-operated means for manually and adjustably moving said systolic indicator means along a second path spaced from and adjacent to said first path;
   (g) second user-operated means for manually and adjustably moving said diastolic indicator means along a third path spaced from and adjacent to both said first and said second paths; and
   (h) each of said indicator means includes means for indicating a single value of blood pressure, and means for simultaneously indicating a range of values of blood pressure; whereby the user either manually presets each of said indicator means to respective positions corresponding to predetermined medically-established pressure norms for subsequent comparison purposes during the blood pressure measurement, or manually sets each of said indicator means to its respective pressure measuring position as observed during the blood pressure measurement for subsequent leisurely recordation.

2. The sphygmomanometer gauge as defined in claim 1, wherein said range-indicating means of said systolic indicator means is operative for indicating a wider range of values as compared to the range indicated by said range-indicating means of said diastolic indicator means.

3. The sphygmomanometer gauge as defined in claim 2, wherein said wider range indicated by said systolic indicator means is on the order of two times as large as the range indicated by said diastolic indicator means.

4. The sphygmomanometer gauge as defined in claim 1, wherein said pressure needle is mounted for turning movement about an axis; and wherein each of said user-operated means includes an adjustable member turnable in either circumferential direction about said axis, and wherein each of said indicator means is mounted on a respective adjustable member for turning movement with the same.

5. The sphygmomanometer gauge as defined in claim 4, wherein each adjustable member has an access portion extending outwardly of said housing to thereby permit ready access and independent manual turning of one adjustable member relative to the other adjustable member.

6. The sphygmomanometer gauge as defined in claim 5, wherein each access portion has a roughened exterior surface to facilitate manual turning of the respective annular member.

7. The sphygmomanometer gauge as defined in claim 4, wherein said first, second and third paths surround said axis and are all concentric with each other.

8. The sphygmomanometer gauge as defined in claim 4, wherein each adjustable member has an upstanding axially-extending portion having a generally circular rim, said rim of one of the adjustable members being spaced radially from said rim of the other of the adjustable members; and wherein each of said indicator means includes colored zones on the respective rims.

9. The sphygmomanometer gauge as defined in claim 8, wherein each rim is of a predetermined color; and wherein said range-indicating means constitutes a generally rectangular-shaped zone having a color which contrasts with said predetermined color, said rectangular-shaped zone also having a pair of radially extending side edges which indicate the outer limits of the respective range; and wherein said single value-indicating means constitutes a generally triangular-shaped zone having a color which contrasts with the color of said rectangular-shaped zone, said triangular-shaped zone lying within said rectangular-shaped zone and being located intermediate said side edges.

10. The sphygmomanometer gauge as defined in claim 4, wherein each adjustable member has an upstanding axially-extending portion having a generally circular rim, said rim of one of the adjustable members being spaced radially from said rim of the other of the adjustable members; and wherein said range-indicating means of one of said indicator means constitutes an axially-extendng, generally parallelepiped-shaped flange portion having a pair of side walls which indicate the outer limits of the respective range; and wherein said range-indicating means of the other of said indicator means constitutes a radially-extending, generally parallelepiped-shaped flange portion having a pair of side walls which indicate the outer limits of the respective range; and wherein each of said single value-indicating means constitutes a radially-extending, generally triangular-shaped flange portion of one-piece both with the respective parallelepiped-shaped flange portion and with the respective rim; and wherein said one indicator means is at a higher elevation than said other indicator means as measured relative to said dial to thereby provide mechanical clearance during turning movement of said adjustable members.

11. The sphygmomanometer gauge as defined in claim 10, wherein the respective side walls of each parallelepiped-shaped portion are spaced apart at a predetermined distance, and wherein the respective triangular-shaped portion has a base wall which extends fully over said predetermined distance.

12. The sphygmomanometer gauge as defined in claim 10, wherein the respective side walls of each parallelepiped-shaped portion are spaced apart at a predetermined distance, and wherein the respective triangular-shaped portion has a base wall which extends over a part of said predetermined distance.

13. The sphygmomanometer gauge as defined in claim 4, wherein each adjustable member includes a crystal mounted on the latter in juxtaposed stacked relationship relative to said dial, and wherein each of said indicator means includes a colored zone on the respective crystal.

14. The sphygmomanometer gauge as defined in claim 13, wherein each colored zone includes a generally rectangular area which constitutes said range-indicating means and which has a pair of radially-extending side edges which indicates the outer limits of the respective range, and a generally radially-extending triangular area which constitutes said single value-indicating means; and wherein said indicator means on one of said crystals is at a higher elevation than said indicator means on the other of said crystals as measured relative to said dial to thereby prevent mechanical interference during turning movement of said adjustable members.

15. The sphygmomanometer gauge as defined in claim 4; and further comprising means for generating a slight frictional drag and a concomitant clicking-type sound during movement of each adjustable member, said generating means including a pair of sets of teeth, each set having a plurality of teeth arranged along an annulus on a respective adjustable member, and a pair of annular pawl plates each having a plurality of resilient spring pawls spaced in circumferential direction about the respective plate, each spring pawl camming in a respective tooth due to its inherent resilience to thereby lock the respective adjustable member in position with a moderate restoring force, and thereupon camming out of the respective tooth when the respective adjustable member is turned in either requisite circumferential direction with a turning force greater than said moderate restoring force.

16. The sphygmomanometer gauge as defined in claim 15; and further comprising means for anchoring said pawl plates, including a crystal mounted in juxtaposed relationship relative to said dial and having a plurality of mounting legs spaced about said axis, a plurality of stationary mounting blocks spaced about said axis on said housing, each mounting block having a recess in which a respective mounting leg is lodged, and a plurality of projections of one-piece with said mounting legs and extending through a plurality of holes formed in said pawl plates, each projection having a deformable head to thereby secure said pawl plates in fixed position relative to said crystal and said mounting blocks.

17. The sphygmomanometer gauge as defined in claim 4, wherein said adjustable members are mounted one above another in stacked, substantially friction-free relationship, one of said adjustable members having a shoulder on which the other of said adjustable members is slidable with minimum frictional drag.

18. In an apparatus for measuring blood pressure, a sphygmomanometer gauge for indicating systolic and diastolic blood pressures to a user, comprising:
(a) a housing;
(b) a pressure-calibrated dial mounted on said housing;
(c) a movable pressure needle mounted on said housing for movement over said pressure-calibrated dial in response to changes in air pressure generated in the apparatus along a first obstruction-free path in which both a systolic pressure measuring position and a diastolic pressure measuring position are located;
(d) manually-movable systolic indictor means mounted on said housing for movement relative to the latter;
(e) manually-movable diastolic indicator means also mounted on said housing for movement relative to the latter;
(f) first user-operated means for manually and adjustably moving said systolic indicator means kinematically independently of said movable pressure needle along a second path spaced from and adjacent to said first path; and
(g) second user-operated means for manually and adjustably moving said diastolic indicator means kinematically independently of said movable pressure needle along a third path spaced from and adjacent to both said first and said second paths, whereby the user either manually presets each of said indicator means to respective positions corresponding to predetermined medically-established pressure norms for subsequent comparison purposes during the blood pressure measurement, or manually sets each of said indicator means to its respective pressure measuring position as observed during the blood pressure measurement for subsequent leisurely recordation.

19. In a sphygmomanometer, a pressure gauge for indicating systolic and diastolic blood pressures to a user, comprising:
(a) a housing having a side port;
(b) a pressure-calibrated dial mounted on said housing and having a plurality of spaced-apart graduations respectively indicative of different values of blood pressure;
(c) a movable pressure needle mounted on said housing for turning movement about an axis over said pressure-calibrated dial in response to changes in air pressure generated in the sphygmomanometer along a first circular path in which both a systolic pressure measuring position and a diastolic pressure measuring position are located;
(d) manually-movable systolic and manually-movable diastolic indicator means, each mounted on said housing for movement relative to the latter, and each including means for indicating a single value of blood pressure and means for simultaneously indicating a range of values of blood pressure; and
(e) first and second user-operated means for manually and adjustably moving each of said indicator means along respective second and third circular paths spaced from, adjacent to and concentric with said first circular path,
each of said user-operated means being an adjustable member independently turnable in either circumferential direction about said axis, each adjustable member having an access portion extending outwardly of said housing through said side port thereof to thereby permit ready access and independent manual turning of the adjustable members;
whereby the user either manually presets each of said indicator means to respective positions corresponding to predetermined medically-established pressure norms for subsequent comparison purposes during the blood pressure measurement, or manually sets each of said indicator means to its respective pressure measuring position as observed during the blood pressure measurement for subsequent leisurely recordation.

20. In a blood pressure measurement, a method of comparing actual systolic and diastolic blood pressure readings with predetermined medically-established pressure norms, comprising the steps of:

(a) manually presetting a systolic indicator relative to a sphygmomanometer gauge dial to a position corresponding to the predetermined medically-established systolic pressure norm for the user by manually moving the systolic indicator in a kinematically independent relationship relative to the pressure needle of a sphygmomanometer;

(b) manually presetting a diastolic indicator relative to the sphygmomanometer dial to another position corresponding to the predetermined medically-established diastolic pressure norm for the user by manually moving the diastolic indicator in a kinematically independent relationship relative to the pressure needle; and (c) observing the pressure needle of a sphygmomanometer gauge move over the dial along an obstruction-free path between systolic and diastolic pressure measuring positions, whereby the user subsequently compares the observed systolic and diastolic positions of the needle with the preset positions of the systolic and diastolic indicators.

21. In a blood pressure measurement, a method of indicating actual systolic and diastolic blood pressure readings for subsequent leisurely recordation, comprising the steps of:

(a) observing the pressure needle of a sphygmomanometer gauge move over a pressure-calibrated dial thereof along an obstruction-free path in response to changes in air pressure generated during the blood pressure measurement between a systolic and a diastolic pressure measuring position;

(b) manually setting a systolic indicator relative to the dial to the observed systolic pressure measuring position during the blood pressure measurement by moving the systolic indicator in a kinematically independent relationship relative to the pressure needle; and (c) manually setting a diastolic indicator relative to the dial to the observed diastolic pressure measuring position during the blood pressure measurement by moving the diastolic indicator in a kinematically independent relationship relative to the needle, whereby the user refers to the manually set positions of the systolic and diastolic indicators subsequent to the blood pressure measurement for leisurely recordation purposes.

22. In a blood pressure measurement, a method of comparing actual systolic and diastolic blood pressure readings with predetermined medically-established pressure norms, comprising the steps of:

(a) manually presetting a systolic indicator relative to a sphygmomanometer gauge dial to a position corresponding to the predetermined medically-established systolic pressure norm for the user;

(b) manually presetting a diastolic indicator relative to the sphygmomanometer dial to another position corresponding to the predetermined medically-established diastolic pressure norm for the user;

(c) observing the pressure needle of a sphygmomanometer gauge move over the dial between systolic and diastolic pressure measuring positions; and (d) the step of indicating a single value of blood pressure, and simultaneously indicating a range of values of blood pressure for each of said steps of manually presetting said systolic and diastolic indicators;

whereby the user subsequently compares the observed systolic and diastolic positions of the needle with the preset positions of the systolic and diastolic indicators.

23. In a blood pressure measurement, a method of indicating actual systolic and diastolic blood pressure readings for subsequent leisurely recordation, comprising the steps of:

(a) observing the pressure needle of a sphygmomanometer gauge move over a pressure-calibrated dial thereof in response to changes in air pressure generated during the blood pressure measurement between a systolic and a diastolic pressure measuring position;

(b) manually setting a systolic indicator relative to the dial to the observed systolic pressure measuring position during the blood pressure measurement;

(c) manually setting a diastolic indicator relative to the dial to the observed diastolic pressure measuring position during the blood pressure measurement; and (d) indicating a single value of blood pressure, and simultaneously indicating a range of values of blood pressure for each of said steps of manually setting said systolic and diastolic indicators;

whereby the user refers to the manually set positions of the systolic and diastolic indicators subsequent to the blood pressure measurement for leisurely recordation purposes.

* * * * *